US008546525B2

(12) United States Patent
Grötzinger (10) Patent No.: US 8,546,525 B2
(45) Date of Patent: Oct. 1, 2013

(54) CHIMERIC HUMAN BETA DEFENSINS (75) Inventor: Joachim Grötzinger, Altwittenbek (DE)

(73) Assignee: Christian-Albrechts-Universität zu Kiel, Kiel (DE)

( * ) Notice: Subject to any disclaimer, the term of this patent is extended or adjusted under 35 U.S.C. 154(b) by 0 days.

(21) Appl. No.: 13/522,094

(22) PCT Filed: Nov. 20, 2010

(86) PCT No.: PCT/DE2010/001365
§ 371 (c)(1),
(2), (4) Date: Oct. 18, 2012

(87) PCT Pub. No.: WO2011/085704
PCT Pub. Date: Jul. 21, 2011

(65) Prior Publication Data
US 2013/0028939 A1   Jan. 31, 2013

(30) Foreign Application Priority Data
Jan. 14, 2010   (DE) .......................... 10 2010 004 541

(51) Int. Cl.
*A61K 38/00* (2006.01)
(52) U.S. Cl.
CPC ..................................... *A61K 38/00* (2013.01)
USPC .......................................................... 530/300
(58) Field of Classification Search
None
See application file for complete search history.

(56) References Cited

FOREIGN PATENT DOCUMENTS
WO    WO 2009/983249 A2 *   7/2009

OTHER PUBLICATIONS

Peptide Sequence for HBD-1, copyright 2002-2001, AnaSpec, Inc., accessed May 9, 2013 from http://www.anaspec.com/products/product.as;?id=32254.*
Diamond, G, Zasloff, M, Eck, H, Brasseur, M, Maloy, WL, Bevins, CL. (1991) Tracheal antimicrobial peptide, a cysteine-rich peptide from mammalian tracheal mucosa: peptide isolation and cloning of a cDNA. Proc Natl Acad Sci USA. 88, 3952-3956.
Ganz, T, Selsted, ME, Szklarek, D, Harwig, SS, Daher, K, Bainton, DF, Lehrer, RI. (1985) Defensins. Natural peptide antibiotics of human neutrophils. J Clin Invest. 76, 1427-1435.
Ganz, T. (2005) Defensins and other antimicrobial peptides: a historical perspective and an update. Comb Chem High Throughput Screen. 8, 209-217.
Garcia, JR, Jaumann, F, Schulz, S, Krause, A, Rodriguez-Jimenez, J, Forssmann, U, Adermann, K, Kluver, E, Vogelmeier, C, Becker, D, Hedrich, R, Forssmann, WG, Bals, R. (2001) Identification of a novel, multifunctional beta-defensin (human beta-defensin 3) with specific antimicrobial activity. Its interaction with plasma membranes of *Xenopus* oocytes and the induction of macrophage chemoattraction. Cell Tissue Res. 306, 257-264.
Garcia, JR, Krause, A, Schulz, S, Rodriguez-Jimenez, FJ, Kluver, E, Adermann, K, Forssmann, U, Frimpong-Boateng, A, Bals, R, Forssmann, WG. (2001) Human beta-defensin 4: a novel inducible peptide with a specific salt-sensitive spectrum of antimicrobial activity. Faseb J. 15, 1819-1821.
Gropp, R, Frye, M, Wagner, TO, Bargon, J. (1999) Epithelial defensins impair adenoviral infection: implication for adenovirus-mediated gene therapy. Hum Gene Ther. 10, 957-964.
Harder, J, Bartels, J, Christophers, E, Schröder, JM. (1997) A peptide antibiotic from human skin. Nature. 387, 861.
Harder, J, Bartels, J, Christophers, E, Schröder, JM. (2001) Isolation and characterization of human beta-defensin-3, a novel human inducible peptide antibiotic. J Biol Chem. 276, 5707-5713.
Harder, J. Meyer-Hoffert, U, Teran, LM, Schwichtenberg, L, Bartels, J, Maune, S, Schroder, JM. (2000) Mucoid *Pseudomonas aeruginosa*, TNF-alpha, and IL-1 beta, but not IL-6, induce human beta-defensin-2 in respiratory epithelia. Am J Respir Cell Mol Biol. 22, 714-721.
Hoover, DM, Chertov, O, Lubkowski, J. (2001) The structure of human beta-defensin-1: new insights into structural properties of beta-defensins. J Biol Chem. 276, 39021-39026.
Hoover, DM, Rajashankar, KR, Blumenthal, R, Puri, A, Oppenheim, JJ, Chertov, O, Lubkowski, J. (2000) The structure of human beta-defensin 2 shows evidence of higher order oligomerization. J Biol Chem. 275, 32911-32918.
Hoover DM, et al., "Antimicrobial characterization of human beta-defensin 3 derivatives," Antimicrob Agents Chemother. Sep. 2003;47(9):2804-9.
Jenssen, H, Hamill, P, Hancock, RE. (2006) Peptide antimicrobial agents. Clin Microbiol Rev. 19, 491-511.
Jia, HP, Schutte, BC, Schudy, A, Linzmeier, R, Guthmiller, JM, Johnson, GK, Tack, BF, Mitros, JP, Rosenthal, A, Ganz, T, McCray, PB, Jr. (2001) Discovery of new human beta-defensin using a genomics-based approach. Gene. 263, 211-218.
Lehrer, RI, Ganz, T. (1996) Endogenous vertebrate antibiotics. Defensins, protegrins, and other cysteine-rich antimicrobial peptides. Ann NY Acad Sci. 797, 228-239.

(Continued)

*Primary Examiner* — Jean C. Witz
*Assistant Examiner* — Mindy Newman
(74) *Attorney, Agent, or Firm* — Meunier Carlin & Curfman, LLC (57) ABSTRACT The invention relates to a nucleic acid molecule selected from the group comprising a) a nucleic acid molecule having one of the nucleotide sequences presented in SEQ ID:NO 4 to SEQ ID:NO 8, b) a nucleic acid molecule that codes for a peptide having one of the amino acid sequences presented in SEQ ID:NO 12 to SEQ ID:NO 16, c) a nucleic acid molecule, the complementary strand of which hybridizes to a nucleic acid molecule according to a) or b) and which codes for a peptide having antimicrobial activity, and d) a nucleic acid molecule, the nucleotide sequence of which deviates from the nucleotide sequence of a nucleic acid molecule according to c) because of the degenerated genetic code.

12 Claims, 2 Drawing Sheets (56) References Cited

OTHER PUBLICATIONS

Li Q, et al., "Potential therapeutic efficacy of a bactericidal-immunomodulatory fusion peptide against methicillin-resistant *Staphylococcus aureus* skin infection," Appl Microbiol Biotechnol. Mar. 2010;86(1):305-9.

Rudolph, B, Podschun, R, Sahly, H, Schubert, S, Schröder, JM, Harder, J. (2006) Identification of RNase 8 as a novel human antimicrobial protein. Antimicrob Agents Chemother. 50, 3194-3196.

Sawai, MV, Jia, HP, Liu, L, Aseyev, V, Wiencek, JM, McCray, PB, Jr., Ganz, T, Kearney, WR, Tack, BF. (2001) The NMR structure of human beta-defensin-2 reveals a novel alpha-helical segment. Biochemistry. 40, 3810-3816.

Schibli, DJ, Hunter, HN, Aseyev, V, Starner, TD, Wiencek, JM, McCray, PB, Jr., Tack, BF, Vogel, HJ. (2002) The solution structures of the human beta-defensins lead to a better understanding of the potent bactericidal activity of HBD3 against *Staphylococcus aureus*. J Biol Chem. 277, 8279-8289.

Schröder, JM. (1999) Epithelial antimicrobial peptides: innate local host response elements. Cell Mol Life Sci. 56, 32-46.

Selsted, ME, Brown, DM, DeLange, RJ, Harwig, SS, Lehrer, RI. (1985) Primary structures of six antimicrobial peptides of rabbit peritoneal neutrophils. J Biol Chem. 260, 4579-4584.

Selsted, ME, Harwig, SS, Ganz, T, Schilling, JW, Lehrer, RI. (1985) Primary structures of three human neutrophil defensins. J Clin Invest. 76, 1436-1439.

Selsted, ME, Harwig, SS. (1989) Determination of the disulfide array in the human defensin HNP-2. A covalently cyclized peptide. J Biol Chem. 264, 4003-4007.

Selsted, ME, Tang, YQ, Morris, WL, McGuire, PA, Novotny, MJ, Smith, W, Henschen, AH, Cullor, JS. (1993) Purification, primary structures, and antibacterial activities of beta-defensins, a new family of antimicrobial peptides from bovine neutrophils. J Biol Chem. 268, 6641 6648.

Singh, PK, Jia, HP, Wiles, K, Hesselberth, J, Liu, L, Conway, BA, Greenberg, EP, Valore, EV, Welsh, MJ, Ganz, T, Tack, BF, McCray, PB, Jr. (1998) Production of beta-defensins by human airway epithelia. Proc Natl Acad Sci USA 95, 14961-14966.

Taylor, K, Barran, PE, Dorin, JR. (2008) Structure-activity relationships in beta-defensin peptides. Biopolymers. 90, 1-7.

Valore, EV, Park, CH, Quayle, AJ, Wiles, KR McCray, PB, Jr., Ganz, T. (1998) Human beta-defensin-1: an antimicrobial peptide of urogenital tissues. J Clin Invest. 101, 1633-1642.

\* cited by examiner

CHIMERIC HUMAN BETA DEFENSINS

REFERENCE TO SEQUENCE LISTING

The Sequence Listing submitted Jul. 24, 2012 as a text file named "10318_002US1_Replacement_Sequence_Listing.txt," created on Jul. 23, 2012, and having a size of 6,637 bytes is hereby incorporated by reference pursuant to 37 C.F.R. §1.52(e)(5).

The invention relates to sequences coding for antimicrobial chimeric peptides from human beta defensin 2 (HBD2) and human beta defensin 3 (HBD3) with a novel antimicrobial activity spectrum, to the antimicrobial peptides encoded by said sequences and their derivatives, and to the use thereof for preparing substances with antimicrobial action and their use.

Antimicrobial peptides have been isolated from a wide variety of organisms, including humans, in whom they are mainly involved in the first line of defense against pathogens (1). Said peptides include the defensins, a family of antimicrobial peptides with a size from 3 to 6 kDa, which have a high proportion of both cationic amino acid residues and cysteine residues (2-5). Their abundance in humans and other vertebrates, together with their microbiocidal activity, rendered them important effector molecules of neutrophiles, mucosal surfaces, skin, and other epithelia (6).

The human defensins are classified into two subfamilies: alpha and beta defensins, which differ in localization and the pairing of six cysteine residues (7-9). Human beta defensins (HBD1-HBD4) are found mainly in various epithelial cells and tissues.

Two of the human beta defensins, HBD2 and HBD3, were originally isolated from keratinocytes of psoriasis patients (10, 11). HBD2 and HBD3 are expressed, apart from in the skin, also in the epithelia of the trachea, lungs, heart muscle and placenta (10, 12, 13). Both molecules are induced due to bacterial influence or proinflammatory cytokines, for example TNFα, interferon-γ and interleukin-1β (10, 12-16).

Most of the evidence of antimicrobial activity of the human beta defensins in vivo comes from experiments in which purified peptides were shown to act on a large number of microorganisms in vitro. HBD1 has antimicrobial action against Gram-positive and Gram-negative bacteria and protects from adenoviral infections (17, 18). HBD2 is active against many Gram-negative bacteria, inter alia *Escherichia coli* and *Pseudomonas aeruginosa*, but also against *Candida albicans*. Moreover, a bacteriostatic action against Gram-positive *Staphylococcus aureus* bacteria has been identified (10). Furthermore, the action of HBD2 against *E. coli* was found to be more potent than that of HBD1 (16). The antimicrobial action of HBD1 and HBD2 depends on the availability of sodium chloride (16). In contrast to those, HBD3 is much more positively charged and has antimicrobial action not only against Gram-negative bacteria but also against Gram-positive bacteria, including *S. aureus* and *Enterococcus faecium* (11, 19). In addition, the bactericidal action of HBD3 is insensitive to the ion concentration (11).

Although the tertiary structures of human beta defensins have been determined, the mechanism of permeabilization of the bacterial double membranes has not been confirmed. Human beta defensins exhibit a characteristic fold composed of three-stranded antiparallel β-sheets and a short N-terminal α-helix (20-23). Structural studies have revealed that both HBD2 and HBD3 can form dimers in solution, in the case of HBD2 only at high peptide concentrations (20, 23). It has been postulated that HBD2 dimers form octamers which, with their structural and electrostatic properties, do not appear to form a membrane-spanning pore. It has been suggested that HBD2 destroys the bacterial membrane due to electrostatic interactions (20). In addition, HBD3 has been shown to generate ion channels in *Xenopus laevis* oocytes (19).

Although the mechanism of action of the defensins has not completely been elucidated, their amphipatic character is believed to be the key to the antimicrobial activity. With the exception of the cysteine residues, conservation of the primary structures within the defensin family is low. It is assumed that the antimicrobial action increases with the net positive charge and the hydrophobicity of the molecule (24).

The primary structures of HBD1-3 suggest that there are considerable differences in the net charge between these defensins. HBD1-3 exhibit a net positive charge of +4, +6 and +11, respectively. Cationic amino acid residues appear in HBD1 and HBD2 mainly downstream of the third cysteine. In HBD3, nine of thirteen cationic amino acid residues are located downstream of this cysteine residue. Said peptides vary in their antimicrobial action. HBD3 shows the most potent activity and the highest positive charge. The importance of the structure for the function has been intensively researched in studies in which the defensin primary structure was modified. Single amino acid substitutions and N-terminal deletions which do not affect the charge or massively alter the hydrophobicity retain the antimicrobial action. These changes may however alter the susceptibility of the bacteria and the killing rate. An increase in net charge and hydrophobicity enhancing the antimicrobial activity is discussed. Peptides having a lower number of cationic residues and moderate hydrophobicity are virtually inactive, while peptides with a high net charge and with significantly hydrophobic character are active. HBD3 has been analyzed in several studies in which various regions of the peptide were comprehensively studied. Synthetic peptides with sequences from the N terminus and the C terminus were prepared. The N-terminal sequence of HBD3, which consists of 17 amino acids and has a net charge of only +4, was synthesized. Despite its low charge, this peptide exhibited antimicrobial activity against Gram-positive and Gram-negative organisms. N-terminal deletion mutants of HBD3 emphasize the importance of the first seven residues for the activity against Gram-positive organisms (24).

There is an urgent need for novel therapeutics in order to successfully control pathogenic microorganisms. In this context, the naturally occurring human beta defensins constitute a protein family with very interesting and different antibiotic properties. As mentioned hereinbefore, HBD2 and HBD3, for example, show remarkable differences in their range of action.

It is therefore an object of the present invention to provide novel peptides which, starting from the natural substances HBD2 and HBD3, can be employed as medicaments having a combined and improved biological and therapeutic defensin activity.

According to the invention, this object is achieved by chimeras of HBD2 and HBD3 having the features of claim 1. The subclaims describe advantageous embodiments of the invention.

The nucleic acid sequences set forth under SEQ ID:NO 3 to SEQ ID:NO 8 code for novel peptides, the HBD2/HBD3 chimeras HBDC1 to C6 (amino acid sequences: SEQ ID:NO 11 to SEQ ID:NO 16). The peptides of the invention, HBDC3 and C5, have a unique activity against *E. coli* and *S. aureus* (see Table 1): they are surprisingly at least as effective as or even more effective than the naturally occurring defensins, HBD2 and HBD3, against said pathogens.

The structural determining factors responsible for the various activities of HBD2 and HBD3 against Gram-positive and Gram-negative bacteria were examined by generating six chimeric molecules from HBD2 and HBD3 and determining their activity against *E. coli* and *S. aureus* strains.

Figure 1:
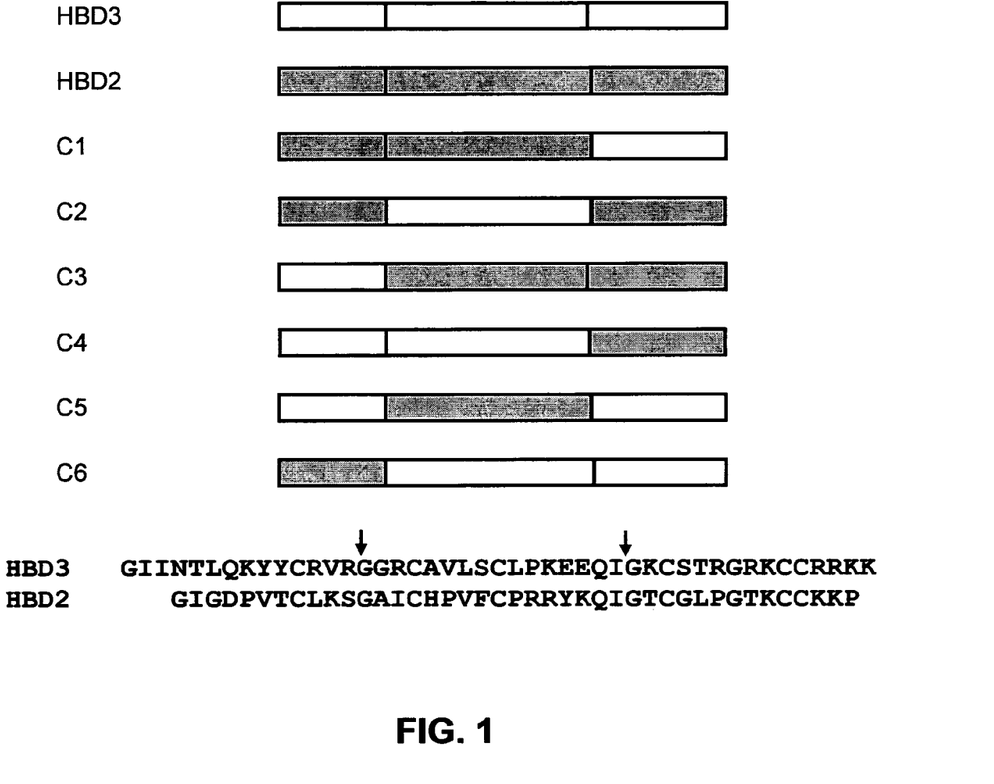
FIG. 1 depicts a diagrammatic representation of the structures of the HBD2/HBD3 chimeras (C1-C6) and a sequence comparison between HBD2 and HBD3.

In HBD2 and HBD3, not only the beta defensin-typical cysteine residues but also two glycine residues are conserved (see FIG. 1). The three dimensional structure of the two defensins showed that these glycine residues are located in loop regions (21, 23).

The sequences of HBD2 (nucleotide sequence SEQ ID:NO 1; protein sequence SEQ ID:NO 9) and HBD3 (nucleotide sequence SEQ ID:NO 2; protein sequence SEQ ID:NO 10) were divided into three domains, with the conserved glycine residues (see arrows in FIG. 1) serving as internal boundary between the different regions for composition of the chimeric peptides of the invention. Thus, the various possible combinations of the three regions produced the following peptides (cf. FIG. 1):

HBDC1: nucleotide sequence SEQ ID:NO 3; protein sequence SEQ ID:NO 11

HBDC2: nucleotide sequence SEQ ID:NO 4; protein sequence SEQ ID:NO 12

HBDC3: nucleotide sequence SEQ ID:NO 5; protein sequence SEQ ID:NO 13

HBDC4: nucleotide sequence SEQ ID:NO 6; protein sequence SEQ ID:NO 14

HBDC5: nucleotide sequence SEQ ID:NO 7; protein sequence SEQ ID:NO 15

HBDC6: nucleotide sequence SEQ ID:NO 8; protein sequence SEQ ID:NO 16

Interestingly, the three domains produced by dividing HBD2 and HBD3 at the conserved glycine residues form a single, self-contained epitope on the molecular surface.

Figure 2:
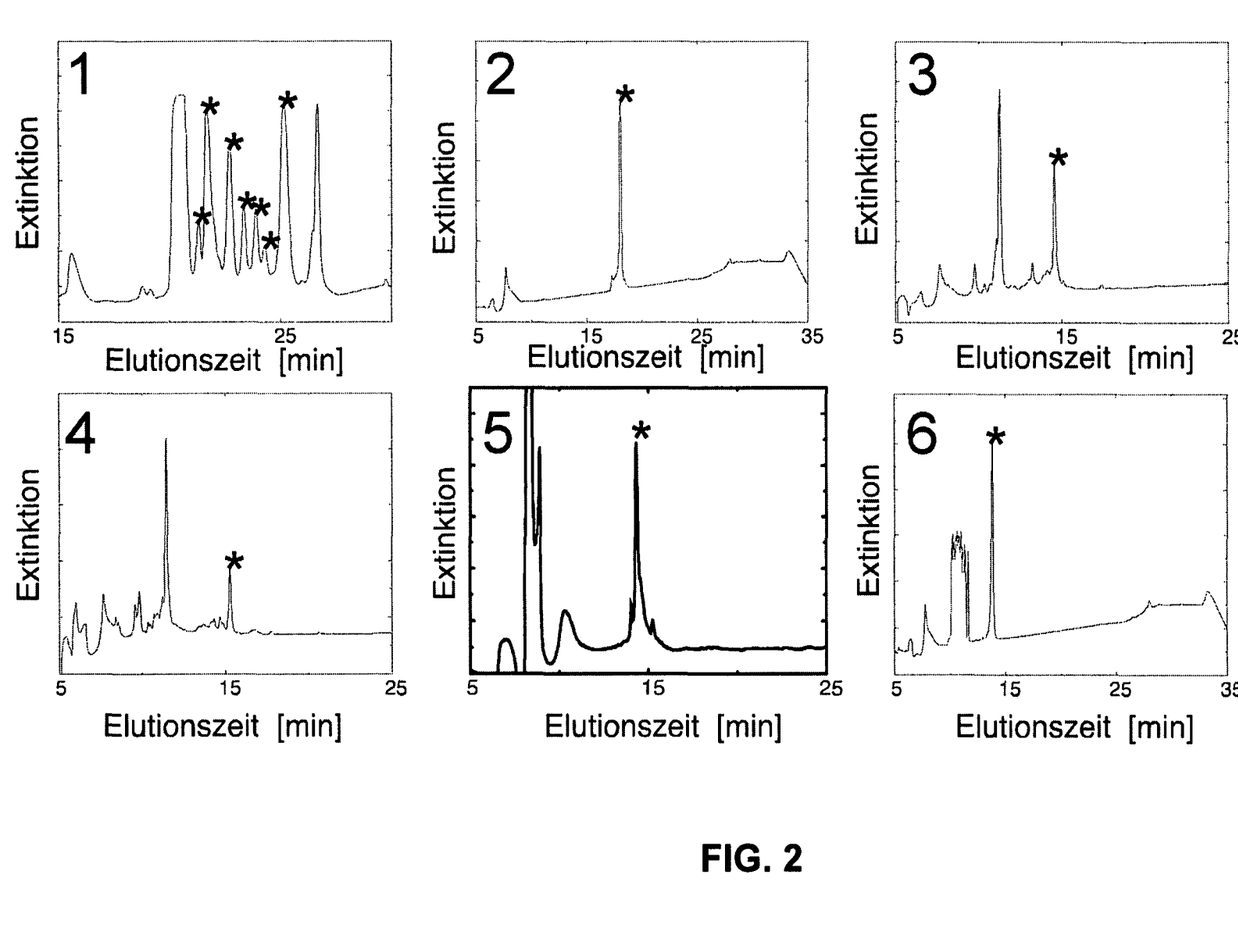
FIG. 2 depicts the result of chromatographic purification of the recombinant HBD2/HBD3 chimeras.

The chimeras of the invention were expressed by way of fusion proteins, as described in the examples. After cleavage of the fusion proteins and purification by RP-HPLC (FIG. 2), the various fractions were analyzed by means of MALDI-TOF. The HPLC fractions corresponding to the expected masses of the peptides are indicated by * in FIG. 2. The HBDC1 chimera was detected in seven different fractions, all of which having the same expected mass (peptides HBDC1.1-1.7). The remaining chimeras, HBDC2, 3, 4, 5 and 6, were eluted by way of a single fraction having the expected mass. The different elution times are probably related to a different linkage of the cysteine side chains in the various molecules.

The antimicrobial activity of the chimeras of the invention against *E. coli* (ATCC 35218) and *S. aureus* (ATCC 12600) was determined and compared to the activity of HBD2 and HBD3 (Table 1). Surprisingly, HBDC3 turns out to have a higher activity against both strains than HBD2, HBD3 and any other chimeras of the invention (with the exception of the minimal bactericidal concentration of HBDC5 against *S. aureus*). The higher activity of HBDC3 compared to the other peptides tested cannot be explained on the basis of the net charge of the protein. The theoretical value at pH 7 is 8.8 for HBDC3 and is thus the same as the value for the less active HBDC4 and lower than the value for the likewise less active HBD3 and HBDC1 (Table 1). After HBDC3, the chimeric peptide with the highest net charge, HBDC5, proves to be exactly as effective as HBD2 and even better than HBD3 against *E. coli* and more effective than both natural defensins against *S. aureus*.

The invention relates in addition to the peptides described also to their biologically active fragments. Biologically active means said fragments have a minimal bactericidal concentration (MBC) which is up to ten times higher than that of the complete peptides on which they are based, according to the measurement method specified in the examples. Preferably, they are derivatives which lack one or more amino acids N- or C-terminal. It is also possible, however, that amino acids have been deleted from the sequence. Such fragments have preferably no more than 30% deleted amino acids.

The invention furthermore relates to those peptides in which individual amino acids have been substituted. Said substitutions are preferably conservative, i.e. amino acids with similar properties are replaced, for example alanine with serine, leucine with isoleucine, etc. Here too, preference is given to replacing no more than 10% of the amino acids in the peptides.

In addition, individual amino acids may also be replaced with non-natural amino acids, i.e. with amino acids carrying further functional groups, for example hydroxyproline, methylthreonine, homocysteine, etc. In this case too, preference is given to no more than 10% of the amino acids being modified accordingly.

Furthermore, the peptides may have derivatizations, they may be, for example, amidated, glycosylated, acetylated, sulfated or phosphorylated.

The present invention furthermore provides a method of preparing the peptides of the invention. Apart from genetically engineering said peptides, constructive total synthesis on customary solid phases in accordance with the Merrifield synthesis or a liquid phase synthesis is also possible. The synthesis strategy and construction of the peptides and of derivatives derived therefrom with the appropriately protected amino acids are known to the skilled worker.

The present invention also relates to the use of the peptides of the invention as medicaments for various therapeutic indications. For this purpose, the peptides may be used as highly pure substances or—if sufficient for said use—within a partly purified peptide mixture or by way of a mixture of a plurality of peptides of the invention.

In addition, the peptides of the invention are also useful for coating surfaces of materials which are intended to be kept as sterile as possible and more specifically ought not to be colonized by bacteria, for example medical instruments, catheters, medical implants or contact lenses.

The invention is described in more detail on the basis of the following examples.

EXAMPLE 1

Generation of Chimeric HBD2 and HBD3 Constructs

The nucleotide sequences of the HBD2/HBD3 chimeras were codon-optimized for bacterial expression (SEQ ID:NO 3-8) and synthesized by GENEART. Said nucleotide sequences were cloned into the expression vector pET/30a (Novagen) using the KspI and XhoI restriction cleavage sites, in order to generate a fusion protein with an N-terminal $(His)_6$ tag and an enterokinase or a factor Xa restriction cleavage site. The sequences of the chimeric peptides fused to the $(His)_6$ tag and an enterokinase or a factor Xa restriction cleavage site are depicted below. The underlined sequences belong to the HBD2/HBD3 chimeras.

```
Peptide 1 (includes HBDC1):
MHHHHHHSSGLVPRGSGMKETAAAKFERQHMDSPDLGTDDDDKGIGDPVT

CLKSGAICHPVFCPRRYKQIGKCSTRGRKCCRRKK

Peptide 2 (includes HBDC2):
MHHHHHHSSGLVPRGSGMKETAAAKFERQHMDSPDLGTDDDDKGIGDPVT

CLKSGGRCAVLSCLPKEEQIGTCGLPGTKCCKKP

Peptide 3 (includes HBDC3):
MHHHHHHSSGLVPRGSGMKETAAAKFERQHMDSPDLGTIEGRGIINTLQK

YYCRVRGAICHPVFCPRRYKQIGTCGLPGTKCCKKP

Peptide 4 (includes HBDC4):
MHHHHHHSSGLVPRGSGMKETAAAKFERQHMDSPDLGTIEGRGIINTLQK

YYCRVRGGRCAVLSCLPKEEQIGTCGLPGTKCCKKP

Peptide 5 (includes HBDC5):
MHHHHHHSSGLVPRGSGMKETAAAKFERQHMDSPDLGTIEGRGIINTLQK

YYCRVRGAICHPVFCPRRYKQIGKCSTRGRKCCRRKK

Peptide 6 (includes HBDC6):
MHHHHHHSSGLVPRGSGMKETAAAKFERQHMDSPDLGTDDDDKGIGDPVT

CLKSGGRCAVLSCLPKEEQIGKCSTRGRKCCRRKK.
```

EXAMPLE 2

Protein Expression

Protein expression was optimal in the following *E. coli* strains: BL21 (DE3) pLys (peptide 1, peptide 2 and peptide 6), Bl21 (DE3) (peptide 4 and peptide 5) and BLR (DE3) (peptide 3). All strains were cultured in LB medium containing 50 µg/ml kanamycin at 37° C. When the cell cultures reached an $OD_{600}$ of between 0.5 and 0.6, IPTG was added to the culture to a final concentration of 1 mM or 0.3 mM (peptide 2) to induce protein expression. The cells were then cultured for another 3 hours, with the exception of the peptide 2 culture which was incubated for 12 hours.

EXAMPLE 3

Purification of Recombinantly Expressed Peptides

The bacteria were harvested by centrifugation at 8000 g and suspended in 50 mM Tris-HCl, 150 mM NaCl, pH 7.5. The bacterial suspension was then sonicated using a Sonopuls HD 2200 instrument (20 kHz, 200 W) equipped with an MS-73 titanium microtip (Bandelin electronic GmbH) (60% duty cycle, 35% power, 1-1.5 min on ice), in order to disrupt the cell membranes. After centrifugation of the cell lysates at 15000 g for 30 min, the peptides were obtained either in soluble form (peptides 1, 2 and 4) or as insoluble inclusion bodies (peptides 3, 5 and 6).

The soluble peptides (1, 2 and 4) in the supernatant were applied to $Ni^{2+}$-NTA agarose columns which were equilibrated with 50 mM sodium phosphate, 300 mM NaCl, 10 mM imidazole, pH 8. The columns were washed with 50 mM sodium phosphate, 300 mM NaCl, 40 mM imidazole, pH 8.0, to remove unspecifically bound proteins. The peptides were then eluted with 50 mM sodium phosphate, 300 mM NaCl, 250 mM imidazole, pH 8. The fractions containing the peptides were collected and concentrated using a 3000 MWCO Vivaspin 20 concentrator.

The insoluble inclusion bodies (peptides 3, 5 and 6) were suspended in 100 mM Tris-HCl, 6 M GdnHCl, pH 8, and applied to $Ni^{2+}$-NTA agarose columns which were equilibrated with 100 mM Tris-HCl, 6 M GdnHCl, pH 8.

The columns were washed with 100 mM Tris-HCl, 6 M GdnHCl, pH 8, and elution was carried out with 6 M GdnHCl, 50 mM sodium acetate, pH 4. The eluted fractions were collected, and refolding of the peptides was carried out by diluting the protein samples to a final concentration of 0.15 mg/ml at 1 M GdnHCl. The redox system (final concentration: 4 mM reduced and 0.4 mM oxidized glutathione) was added, and the pH was adjusted to 8.5. The samples were incubated at 4° C. for 72 h and then centrifuged at 18000 g for 30 min and concentrated.

EXAMPLE 4

Cleavage of the Peptides by Enterokinase or Factor Xa

Prior to cleavage, the peptides (in 1M GdnHCl, pH 8.5) were applied to an NAP 10 column in order to replace the buffer with 50 mM sodium phosphate, 200 mM NaCl, pH 7.8 (cleavage buffer). The cleavage was carried out at room temperature overnight.

EXAMPLE 5

Purification of the Cleaved Peptides by HPLC

After cleavage, all peptides were purified by HPLC using a VP 250/10 Nucleosil 300-7 C18 reverse phase HPLC column (Macherey Nagel) connected to a VP 50/10 Nucleosil 300-7 C18 reverse phase HPLC precolumn. Absorbance was measured at 214 nm. The fractions were collected manually in order to keep the various forms of peptides separate. All samples were adjusted to an acidic pH before being applied to the column. The gradients consisted of buffer A (2% ACN in 0.1% TFA) and B (95% ACN in 0.1% TFA). The following gradients were used for purification of the peptides:

- HBDC1: 2 min. 80% A, 10 min. 80% A, 20 min. 70% A, 23 min. 0% A, 28 min. 0% A, 33 min. 100% A, 38 min. 100% A.
- HBDC2: 2 min. 80% A, 20 min. 36% A, 22 min. 0% A, 27 min. 0% A, 32 min. 100% A, 37 min. 100% A.
- HBDC3: 2 min. 80% A, 20 min. 25% A, 22 min. 0% A, 27 min. 0% A, 32 min. 100% A, 37 min. 100% A.
- HBDC4: 2 min. 80% A, 20 min. 25% A, 22 min. 0% A, 27 min. 0% A, 32 min. 100% A, 37 min. 100% A.
- HBDC5: 3 min. 69% A, 10 min. 69% A, 20 min. 68% A, 30 min. 68% A, 34 min. 0% A, 39 min. 0% A, 44 min. 100% A, 49 min. 100% A.
- HBDC6: 2 min. 80% A, 20 min. 36% A, 22 min. 0% A, 27 min. 0% A, 32 min. 100% A, 37 min. 100% A.

EXAMPLE 6

Determination of Protein Concentration

Extinction at 214 nm was measured for the various peptides, and the protein concentration was determined on the basis of the following extinction coefficients:

- HBDC1: $\epsilon_{214}=138805\ M^{-1}\ cm^{-1}$;
- HBDC2: $\epsilon_{214}=116686\ M^{-1}\ cm^{-1}$;
- HBDC3: $\epsilon_{214}=161699\ M^{-1}\ cm^{-1}$;
- HBDC4: $\epsilon_{214}=142426\ M^{-1}\ cm^{-1}$;
- HBDC5: $\epsilon_{214}=158853\ M^{-1}\ cm^{-1}$;
- HBDC6: $\epsilon_{214}=122378\ M^{-1}\ cm^{-1}$.

EXAMPLE 7

Mass Spectrometry

The average mass of the derivatives of the purified peptides were determined by means of matrix-assisted laser desorption ionization time of flight mass spectrometry (MALDI- TOF MS). The samples were mixed with the matrix solution (8 mg/ml α-cyanocinnamic acid in 60% acetonitrile/0.1% trifluoroacetic acid) and applied to a stainless steel support. The mass spectra were recorded in positive ion linear mode using a MALDI-TOF/TOF mass spectrometer (4700 Proteomics Analyzer, Applied Biosystems, Framingham, Mass., USA). Internal calibration of the instrument was carried out prior to each measurement. The average mass of the proteins were compared to the theoretical average mass of the derivatives taking into account potential disulfide formation.

EXAMPLE 8

Molecular Modeling

Models of the three dimensional structure of the HBD2/HBD3 chimeras were produced using the structures of HBD2 (pdb accession code: 1e4q) and HBD3 (pdb accession code: 1kj6) as templates. The positions of the six cysteine residues in each molecule were used for superimposing the two structures. The important parts were taken from each structure and combined to give the chimeric molecules.

EXAMPLE 9

Antimicrobial Activity

The antimicrobial activity of the peptides was determined on the basis of a modified microdilution experiment, as described previously (25). Briefly, after growth in brain heart infusion broth at 36±1° C. for 2-3 h, the bacterial suspensions were adjusted to $10^4$ to $10^5$ bacteria/ml in 10 mM sodium phosphate buffer (pH 7.4) containing 1% tryptic soy broth (TSB). In each case, 100 µl of bacterial suspension were admixed with 10 µl of an antimicrobial peptide solution (final concentrations in test: 0.0125-100 µg/ml) and incubated at 36±–1° C. Colony forming units (CFUs) were determined after 2 h. Bacterial suspensions admixed with 10 µl of phosphate buffer/1% TSB or with 10 ml of 0.01% acetic acid rather than with peptide solution were used as negative control. The antibacterial activities of the peptides are indicated as $LD_{90}$ (90% lethal dose, concentrations that are lethal for 90% of the microorganisms) or as MBCs (minimal bactericidal concentrations; 99.9% killing). A bacterial strain was arbitrarily defined as sensitive to a peptide at MBCs of 12.5 µg/ml, as moderately sensitive at 25<MBC<100 µg/ml, and as resistant at MBCs of >100 µg/ml.

TABLE 1

Antimicrobial activity and net charge at pH 7 of HBD2, HBD3 and HBD2/HBD3 chimeras HBDC1-6.

| Protein | E. coli ATCC 35218 | | S. aureus ATCC 12600 | | Net charge (pH 7) |
|---|---|---|---|---|---|
| | $LD_{90}$ [µg/ml] | MBC [µg/ml] | $LD_{90}$ [µg/ml] | MBC [µg/ml] | |
| HBD2 | 0.1 | 0.39 | 1.56 | 12.5 | +5.8 |
| HBD3 | 0.39 | 1.56 | 0.15 | 1.19 | +10.7 |
| 1.1 | 0.1 | 0.2 | 0.78 | 6.25 | +10.8 |
| 1.2 | 0.025 | 0.1 | 0.39 | 3.125 | +10.8 |
| 1.3 | 0.025 | 0.1 | 0.39 | 1.56 | +10.8 |
| 1.4 | 0.025 | 0.2 | 0.78 | 3.125 | +10.8 |
| 1.5 | 0.025 | 0.1 | 0.39 | 6.25 | +10.8 |
| 1.6 | 0.025 | 0.2 | 3.125 | 6.25 | +10.8 |
| 1.7 | 0.05 | 0.2 | 0.39 | 6.25 | +10.8 |
| 2 | 0.39 | n.d. | >100 | >100 | +2.7 |
| 3 | 0.025 | 0.1 | 0.1 | 0.78 | +8.8 |

TABLE 1-continued

Antimicrobial activity and net charge at pH 7 of HBD2, HBD3 and HBD2/HBD3 chimeras HBDC1-6.

| Protein | E. coli ATCC 35218 | | S. aureus ATCC 12600 | | Net charge (pH 7) |
|---|---|---|---|---|---|
| | $LD_{90}$ [µg/ml] | MBC [µg/ml] | $LD_{90}$ [µg/ml] | MBC [µg/ml] | |
| 4 | 1.56 | 6.25 | 0.39 | 3.125 | +8.8 |
| 5 | 0.1 | 0.39 | 0.1 | 0.39 | +13.8 |
| 6 | n.d. | >100 | >100 | >100 | +7.7 |

MBC: minimal bactericidal concentration (concentration at which more than 99.9% of bacteria are killed)
LD 90: lethal dose for 90% of cells
n.d.: not determined

LITERATURE (1) Jenssen, H, Hamill, P, Hancock, R E. (2006) Peptide antimicrobial agents. *Clin Microbiol Rev.* 19, 491-511.
(2) Ganz, T, Selsted, M E, Szklarek, D, Harwig, S S, Daher, K, Bainton, D F, Lehrer, R I. (1985) Defensins. Natural peptide antibiotics of human neutrophils. *J Clin Invest.* 76, 1427-1435.
(3) Selsted, M E, Brown, D M, DeLange, R J, Harwig, S S, Lehrer, R I. (1985) Primary structures of six antimicrobial peptides of rabbit peritoneal neutrophils. *J Biol Chem.* 260, 4579-4584.
(4) Selsted, M E, Harwig, S S, Ganz, T, Schilling, J W, Lehrer, R I. (1985) Primary structures of three human neutrophil defensins. *J Clin Invest.* 76, 1436-1439.
(5) Diamond, G, Zasloff, M, Eck, H, Brasseur, M, Maloy, W L, Bevins, C L. (1991) Tracheal antimicrobial peptide, a cysteine-rich peptide from mammalian tracheal mucosa: peptide isolation and cloning of a cDNA. *Proc Natl Acad Sci USA.* 88, 3952-3956.
(6) Lehrer, R I, Ganz, T. (1996) Endogenous vertebrate antibiotics. Defensins, protegrins, and other cysteine-rich antimicrobial peptides. *Ann NY Acad Sci.* 797, 228-239.
(7) Ganz, T. (2005) Defensins and other antimicrobial peptides: a historical perspective and an update. *Comb Chem High Throughput Screen.* 8, 209-217.
(8) Selsted, M E, Harwig, S S. (1989) Determination of the disulfide array in the human defensin HNP-2. A covalently cyclized peptide. *J Biol Chem.* 264, 4003-4007.
(9) Selsted, M E, Tang, Y Q, Morris, W L, McGuire, P A, Novotny, M J, Smith, W, Henschen, A H, Cullor, J S. (1993) Purification, primary structures, and antibacterial activities of beta-defensins, a new family of antimicrobial peptides from bovine neutrophils. *J Biol Chem.* 268, 6641-6648.
(10) Harder, J, Bartels, J, Christophers, E, Schröder, J M. (1997) A peptide antibiotic from human skin. *Nature.* 387, 861.
(11) Harder, J, Bartels, J, Christophers, E, Schröder, J M. (2001) Isolation and characterization of human beta-defensin-3, a novel human inducible peptide antibiotic. *J Biol Chem.* 276, 5707-5713.
(12) Garcia, J R, Krause, A, Schulz, S, Rodriguez-Jimenez, F J, Kluver, E, Adermann, K, Forssmann, U, Frimpong-Boateng, A, Bals, R, Forssmann, W G. (2001) Human beta-defensin 4: a novel inducible peptide with a specific salt-sensitive spectrum of antimicrobial activity. *Faseb J.* 15, 1819-1821.
(13) Jia, H P, Schutte, B C, Schudy, A, Linzmeier, R, Guthmiller, J M, Johnson, G K, Tack, B F, Mitros, J P, Rosenthal, A, Ganz, T, McCray, P B, Jr. (2001) Discovery of new human beta-defensin using a genomics-based approach. *Gene.* 263, 211-218.

(14) Schröder, J M. (1999) Epithelial antimicrobial peptides: innate local host response elements. *Cell Mol Life Sci.* 56, 32-46.

(15) Harder, J. Meyer-Hoffert, U, Teran, L M, Schwichtenberg, L, Bartels, J, Maune, S, Schröder, J M. (2000) Mucoid *Pseudomonas aeruginosa*, TNF-alpha, and IL-1 beta, but not IL-6, induce human beta-defensin-2 in respiratory epithelia. *Am J Respir Cell Mol Biol.* 22, 714-721.

(16) Singh, P K, Jia, H P, Wiles, K, Hesselberth, J, Liu, L, Conway, B A, Greenberg, E P, Valore, E V, Welsh, M J, Ganz, T, Tack, B F, McCray, P B, Jr. (1998) Production of beta-defensins by human airway epithelia. *Proc Natl Acad Sci USA* 95, 14961-14966.

(17) Gropp, R, Frye, M, Wagner, T O, Bargon, J. (1999) Epithelial defensins impair adenoviral infection: implication for adenovirus-mediated gene therapy. *Hum Gene Ther.* 10, 957-964.

(18) Valore, E V, Park, C H, Quayle, A J, Wiles, K R, McCray, P B, Jr., Ganz, T. (1998) Human beta-defensin-1: an antimicrobial peptide of urogenital tissues. *J Clin Invest.* 101, 1633-1642.

(19) Garcia, J R, Jaumann, F, Schulz, S, Krause, A, Rodriguez-Jimenez, J, Forssmann, U, Adermann, K, Kluver, E, Vogelmeier, C, Becker, D, Hedrich, R, Forssmann, W G, Bals, R. (2001) Identification of a novel, multifunctional beta-defensin (human beta-defensin 3) with specific antimicrobial activity. Its interaction with plasma membranes of *Xenopus* oocytes and the induction of macrophage chemoattraction. *Cell Tissue Res.* 306, 257-264.

(20) Hoover, D M, Rajashankar, K R, Blumenthal, R, Puri, A, Oppenheim, J J, Chertov, O, Lubkowski, J. (2000) The structure of human beta-defensin-2 shows evidence of higher order oligomerization. *J Biol Chem.* 275, 32911-32918.

(21) Sawai, M V, Jia, H P, Liu, L, Aseyev, V, Wiencek, J M, McCray, P B, Jr., Ganz, T, Kearney, W R, Tack, B F. (2001) The NMR structure of human beta-defensin-2 reveals a novel alpha-helical segment. *Biochemistry.* 40, 3810-3816.

(22) Hoover, D M, Chertov, O, Lubkowski, J. (2001) The structure of human beta-defensin-1: new insights into structural properties of beta-defensins. *J Biol Chem.* 276, 39021-39026.

(23) Schibli, D J, Hunter, H N, Aseyev, V, Starner, T D, Wiencek, J M, McCray, P B, Jr., Tack, B F, Vogel, H J. (2002) The solution structures of the human beta-defensins lead to a better understanding of the potent bactericidal activity of HBD3 against *Staphylococcus aureus*. *J Biol Chem.* 277, 8279-8289.

(24) Taylor, K, Barran, P E, Dorin, J R. (2008) Structure-activity relationships in beta-defensin peptides. *Biopolymers.* 90, 1-7.

(25) Rudolph, B, Podschun, R, Sahly, H, Schubert, S, Schröder, J M, Harder, J. (2006) Identification of RNase 8 as a novel human antimicrobial protein. *Antimicrob Agents Chemother.* 50, 3194-3196.

The invention claimed is:

1. A nucleic acid molecule selected from the group consisting of
   a) a nucleic acid molecule comprising the nucleotide sequence SEQ ID:NO 4, SEQ ID NO: 5, SEQ ID NO: 6, SEQ ID NO: 7, or SEQ ID:NO 8,
   b) a nucleic acid molecule which encodes a peptide comprising the amino acid sequence SEQ ID:NO 12, SEQ ID NO: 13, SEQ ID NO: 14, SEQ ID NO:15, or SEQ ID:NO 16,
   c) a nucleic acid molecule, the complementary strand of which hybridizes to a nucleic acid molecule according to a) or b) and which encodes a peptide having antimicrobial activity, and
   d) a nucleic acid molecule, the nucleotide sequence of which deviates from the nucleotide sequence of a nucleic acid molecule according to c) owing to the degeneracy of the genetic code.

2. A vector comprising the nucleic acid molecule of claim 1.

3. A host cell comprising the nucleic acid molecule of claim 1.

4. A host cell comprising the vector of claim 2.

5. A peptide comprising the amino acid sequence SEQ ID:NO 12, SEQ ID NO: 13, SEQ ID NO: 14, SEQ ID NO:15, or SEQ ID:NO 16, or a variant thereof comprising conservative amino acid substitutions in no more than 30% of the amino acids.

6. The peptide of claim 5, wherein the peptide is a cyclic, amidated, acetylated, sulfated, phosphorylated, glycosilated or oxidized derivative.

7. The peptide of claim 5, wherein no more than 30% of the amino acids specified have been conservatively substituted by other amino acids.

8. The peptide as claimed in claim 5, wherein no more than 10% of the amino acids specified have been substituted by non-naturally occurring amino acids.

9. The peptide as claimed in claim 8, wherein the non-naturally occurring amino acids are selected from the group consisting of hydroxyproline, methylthreonine or homocysteine.

10. A method for treating a microbial infection in a subject, comprising administering to the subject the peptide of claim 5.

11. The method of claim 10, wherein the microbial infection is a Gram-negative or Gram-positive bacteria.

12. A method, comprising coating the peptide of claim 5 on a medical instrument, a catheter, a medical implant or a contact lens.

* * * * *

```
                        SEQUENCE LISTING

<160> NUMBER OF SEQ ID NOS: 16

<210> SEQ ID NO 1
<211> LENGTH: 125
<212> TYPE: DNA
<213> ORGANISM: Homo sapiens

<400> SEQUENCE: 1
gtggtatagg cgatcctgtt acctgcctta agagtggagc catatgtcat ccagtctttt      60
gccctagaag gtataaacaa attggcacct gtggtctccc tggaacaaaa tgctgcaaaa     120
agcca                                                                 125

<210> SEQ ID NO 2
<211> LENGTH: 148
<212> TYPE: DNA
<213> ORGANISM: Homo sapiens

<400> SEQUENCE: 2
tggaggaatc ataaacacat tacagaaata ttattgcaga gtcagaggcg gccggtgtgc      60
tgtgctcagc tgccttccaa aggaggaaca gatcggcaag tgctcgacgc gtggccgaaa     120
atgctgccga agaaagaaat aaaaaccc                                        148

<210> SEQ ID NO 3
<211> LENGTH: 126
<212> TYPE: DNA
<213> ORGANISM: artificial sequence
<220> FEATURE:
<223> OTHER INFORMATION: synthetic construct

<400> SEQUENCE: 3
ggtattggtg atccggtgac ctgtctgaaa agcggtgcca tttgccatcc ggttttttgc      60
```

-continued

```
ccgcgtcgct ataaacaaat cggcaaatgt agcacccgtg gtcgtaaatg ctgccgtcgt    120
aaaaaa                                                                126

<210> SEQ ID NO 4
<211> LENGTH: 123
<212> TYPE: DNA
<213> ORGANISM: artificial sequence
<220> FEATURE:
<223> OTHER INFORMATION: synthetic construct

<400> SEQUENCE: 4
ggtattggtg atccggtgac ctgtctgaaa agcggtggtc gttgcgcggt tctgagctgt    60
ctgccgaaag aagaacaaat tggcacctgc ggtctgccgg gcaccaaatg ctgtaaaaaa    120
ccg                                                                  123

<210> SEQ ID NO 5
<211> LENGTH: 132
<212> TYPE: DNA
<213> ORGANISM: artificial sequence
<220> FEATURE:
<223> OTHER INFORMATION: synthetic construct

<400> SEQUENCE: 5
ggcattatta acaccctgca gaaatactat tgccgtgttc gtggtgccat ttgccatccg    60
gttttttgcc cgcgtcgcta taaacaaatt ggcacctgtg gtctgccggg caccaaatgc    120
tgtaaaaaac cg                                                        132

<210> SEQ ID NO 6
<211> LENGTH: 132
<212> TYPE: DNA
<213> ORGANISM: artificial sequence
<220> FEATURE:
<223> OTHER INFORMATION: synthetic construct

<400> SEQUENCE: 6
ggcattatta acaccctgca gaaatactat tgccgtgttc gtggtggtcg ttgtgccgtt    60
ctgagctgtc tgccgaaaga agaacaaatt ggcacctgcg gtctgccggg caccaaatgc    120
tgtaaaaaac cg                                                        132

<210> SEQ ID NO 7
<211> LENGTH: 135
<212> TYPE: DNA
<213> ORGANISM: artificial sequence
<220> FEATURE:
<223> OTHER INFORMATION: synthetic construct

<400> SEQUENCE: 7
ggcattatta acaccctgca gaaatactat tgccgtgttc gtggtgccat ttgccatccg    60
gttttttgcc cgcgtcgcta taaacaaatc ggcaaatgta gcacccgtgg tcgtaaatgc    120
tgccgtcgta aaaaa                                                     135

<210> SEQ ID NO 8
<211> LENGTH: 126
<212> TYPE: DNA
<213> ORGANISM: artificial sequence
<220> FEATURE:
<223> OTHER INFORMATION: synthetic construct

<400> SEQUENCE: 8
ggtattggtg atccggtgac ctgtctgaaa agcggtggtc gttgcgcggt tctgagctgt    60
```

```
ctgccgaaag aagaacaaat cggcaaatgt agcacccgtg gtcgtaaatg ctgccgtcgt    120
aaaaaa                                                              126
```

<210> SEQ ID NO 9
<211> LENGTH: 41
<212> TYPE: PRT
<213> ORGANISM: Homo sapiens

<400> SEQUENCE: 9

```
Gly Ile Gly Asp Pro Val Thr Cys Leu Lys Ser Gly Ala Ile Cys His
1               5                   10                  15

Pro Val Phe Cys Pro Arg Arg Tyr Lys Gln Ile Gly Thr Cys Gly Leu
            20                  25                  30

Pro Gly Thr Lys Cys Cys Lys Lys Pro
        35                  40
```

<210> SEQ ID NO 10
<211> LENGTH: 45
<212> TYPE: PRT
<213> ORGANISM: Homo sapiens

<400> SEQUENCE: 10

```
Gly Ile Ile Asn Thr Leu Gln Lys Tyr Tyr Cys Arg Val Arg Gly Gly
1               5                   10                  15

Arg Cys Ala Val Leu Ser Cys Leu Pro Lys Glu Glu Gln Ile Gly Lys
            20                  25                  30

Cys Ser Thr Arg Gly Arg Lys Cys Cys Arg Arg Lys Lys
        35                  40                  45
```

<210> SEQ ID NO 11
<211> LENGTH: 42
<212> TYPE: PRT
<213> ORGANISM: artificial sequence
<220> FEATURE:
<223> OTHER INFORMATION: synthetic construct

<400> SEQUENCE: 11

```
Gly Ile Gly Asp Pro Val Thr Cys Leu Lys Ser Gly Ala Ile Cys His
1               5                   10                  15

Pro Val Phe Cys Pro Arg Arg Tyr Lys Gln Ile Gly Lys Cys Ser Thr
            20                  25                  30

Arg Gly Arg Lys Cys Cys Arg Arg Lys Lys
        35                  40
```

<210> SEQ ID NO 12
<211> LENGTH: 41
<212> TYPE: PRT
<213> ORGANISM: artificial sequence
<220> FEATURE:
<223> OTHER INFORMATION: synthetic construct

<400> SEQUENCE: 12

```
Gly Ile Gly Asp Pro Val Thr Cys Leu Lys Ser Gly Gly Arg Cys Ala
1               5                   10                  15

Val Leu Ser Cys Leu Pro Lys Glu Glu Gln Ile Gly Thr Cys Gly Leu
            20                  25                  30

Pro Gly Thr Lys Cys Cys Lys Lys Pro
        35                  40
```

<210> SEQ ID NO 13
<211> LENGTH: 44

```
<212> TYPE: PRT
<213> ORGANISM: artificial sequence
<220> FEATURE:
<223> OTHER INFORMATION: synthetic construct

<400> SEQUENCE: 13

Gly Ile Ile Asn Thr Leu Gln Lys Tyr Tyr Cys Arg Val Arg Gly Ala
1               5                   10                  15

Ile Cys His Pro Val Phe Cys Pro Arg Arg Tyr Lys Gln Ile Gly Thr
                20                  25                  30

Cys Gly Leu Pro Gly Thr Lys Cys Cys Lys Lys Pro
        35                  40

<210> SEQ ID NO 14
<211> LENGTH: 44
<212> TYPE: PRT
<213> ORGANISM: artificial sequence
<220> FEATURE:
<223> OTHER INFORMATION: synthetic construct

<400> SEQUENCE: 14

Gly Ile Ile Asn Thr Leu Gln Lys Tyr Tyr Cys Arg Val Arg Gly Gly
1               5                   10                  15

Arg Cys Ala Val Leu Ser Cys Leu Pro Lys Glu Glu Gln Ile Gly Thr
                20                  25                  30

Cys Gly Leu Pro Gly Thr Lys Cys Cys Lys Lys Pro
        35                  40

<210> SEQ ID NO 15
<211> LENGTH: 45
<212> TYPE: PRT
<213> ORGANISM: artificial sequence
<220> FEATURE:
<223> OTHER INFORMATION: synthetic construct

<400> SEQUENCE: 15

Gly Ile Ile Asn Thr Leu Gln Lys Tyr Tyr Cys Arg Val Arg Gly Ala
1               5                   10                  15

Ile Cys His Pro Val Phe Cys Pro Arg Arg Tyr Lys Gln Ile Gly Lys
                20                  25                  30

Cys Ser Thr Arg Gly Arg Lys Cys Cys Arg Arg Lys Lys
        35                  40                  45

<210> SEQ ID NO 16
<211> LENGTH: 42
<212> TYPE: PRT
<213> ORGANISM: artificial sequence
<220> FEATURE:
<223> OTHER INFORMATION: synthetic construct

<400> SEQUENCE: 16

Gly Ile Gly Asp Pro Val Thr Cys Leu Lys Ser Gly Arg Cys Ala
1               5                   10                  15

Val Leu Ser Cys Leu Pro Lys Glu Glu Gln Ile Gly Lys Cys Ser Thr
                20                  25                  30

Arg Gly Arg Lys Cys Cys Arg Arg Lys Lys
        35                  40
```